USO05847237A

United States Patent [19]
Yago et al.

[11] Patent Number: 5,847,237
[45] Date of Patent: Dec. 8, 1998

[54] CATALYST FOR ORTHO-ALKYLATION OF PHENOLS, A PRECURSOR THEREOF, AND PRODUCTION OF ORTHO-ALKYLATED PHENOLS BY USE OF SAID CATALYST

[75] Inventors: Shunji Yago; Takashi Kakiuchi; Keiji Arimatsu; Fujihisa Matsunaga, all of Wakayama, Japan

[73] Assignee: Honshu Chemical Industry Co., Ltd., Tokyo, Japan

[21] Appl. No.: 675,497

[22] Filed: Jul. 3, 1996

[51] Int. Cl.⁶ .............................. C07C 37/00; B01J 23/32
[52] U.S. Cl. ........................ 568/804; 568/794; 502/324; 502/156
[58] Field of Search ............................ 568/804, 794; 502/324, 156

[56] References Cited

U.S. PATENT DOCUMENTS 4,528,407  7/1985  Smith et al. .............................. 568/804
4,661,638  4/1987  Battista et al. .......................... 568/804

*Primary Examiner*—Ponnathapura Achutamurthy
*Assistant Examiner*—Hankyel T. Park
*Attorney, Agent, or Firm*—Jacobson, Price, Holman & Stern, PLLC

[57] ABSTRACT

There is disclosed a catalyst for ortho-alkylation of phenols obtained by calcination of a catalyst precursor comprising a dry mixture of:

(a) manganese oxalate;
(b) phenolic resin fine particles; and
(c) at least one magnesium compound selected from the group consisting of basic magnesium carbonate and magnesium hydroxide.

There is further disclosed a process for producing ortho-alkylated phenols by the gas phase reaction between an alkyl alcohol and a phenol in the presence of the ortho-alkylation catalyst defined above.

12 Claims, 1 Drawing Sheet

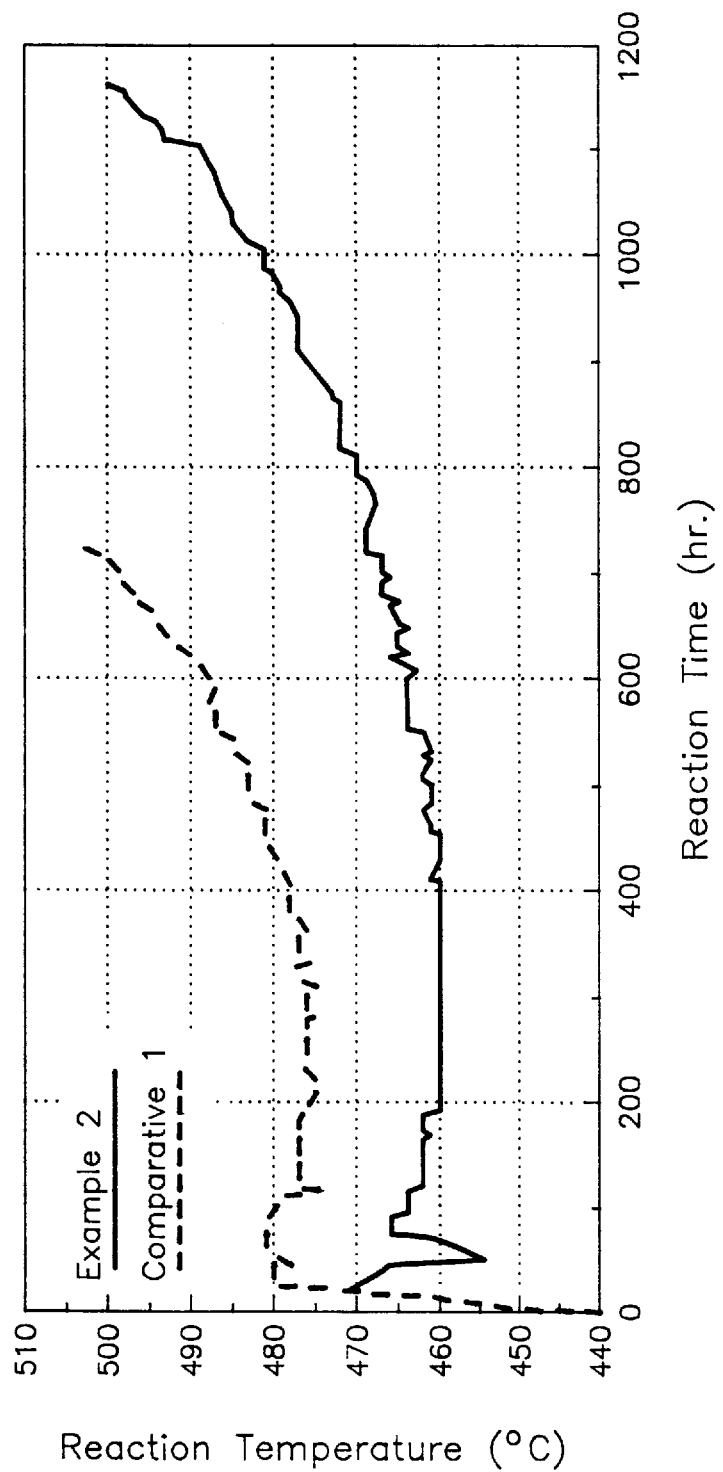

CATALYST FOR ORTHO-ALKYLATION OF PHENOLS, A PRECURSOR THEREOF, AND PRODUCTION OF ORTHO-ALKYLATED PHENOLS BY USE OF SAID CATALYST

BACKGROUND OF THE INVENTION

1. Field of the Invention

The present invention relates to a catalyst for ortho-alkylation of phenols, a precursor thereof, and a process for producing ortho-alkylated phenols by use of said catalyst. More particularly, the invention relates to a process for producing ortho-alkylated phenols by ortho-alkylation of phenols having at least one ortho-hydrogen atom with an alkyl alcohol. A preferred embodiment of the invention relates to a process for producing ortho-methylated phenols by ortho-methylation of phenols having at least one ortho-hydrogen atom with methyl alcohol.

There are phenols having on the aromatic ring a methyl substituent at the ortho position with respect to the hydroxyl group. They are exemplified by 2,6-xylenol, 2,3,6-trimethylphenol, o-cresol, 2,5-xylenol, 2,4-xylenol, 2,3,5-trimethylphenol, or hydroquinone. The first one finds use as a raw material for polyphenyleneoxide resin, the second one finds use as a starting material for synthesis of vitamin E, and the rests are raw materials or intermediates for medicines, agricultural chemicals, additives, and industrial chemicals.

2. Description of the Prior Art

The ortho-alkylation of phenols having at least one ortho-hydrogen atom with an alkyl alcohol in the presence of an alkylating catalyst is already known. The alkylation reaction usually employs magnesium oxide as a catalyst, which may be combined with a manganese salt as a cocatalyst. The reaction is carried out in the gas phase. A catalyst based on magnesium oxide alone is disclosed in Japanese Patent Publication No. 6894/1967. It is obtained from basic magnesium carbonate by compression molding and subsequent calcination. A catalyst composed of magnesium oxide and manganese sulfate is disclosed in Japanese Patent Publication No. 21371/1971. It is prepared by impregnation of magnesium oxide with manganese sulfate, followed by drying, molding, and calcination. Another example of catalyst is disclosed in Japanese Patent Publication Nos. 28784/1977 and 1288/1979. It is prepared from magnesium oxide and silica powder or cellulose polymer (as a binder) by dry mixing, molding, and calcination. Further another example is described in Japanese Patent Publication No. 12337/1968. It is obtained from magnesium oxide by hydration, molding, and calcination.

These prior art technologies indicate that magnesium oxide is derived from magnesium carbonate or magnesium hydroxide by thermal decomposition. It is recommended in Japanese Patent Laid-open No. 99129/1973 that manganese salt as a cocatalyst be a pyrolyzable one such as manganese hydroxide, manganese carbonate, manganese oxalate, or manganese sulfate. In other words, the cocatalyst in the prior art was a manganese salt which is subject to thermal decomposition during calcination of the catalyst precursor at high temperatures.

The catalyst for ortho-alkylation of phenols has recently been greatly improved. An example is disclosed in Japanese Patent Laid-open Nos. 34923/1985 and 155145/1985. The process for the production of the catalyst consists of adding an aqueous solution of manganese sulfate and subsequently ammonium hydroxide to a mixture of basic magnesium carbonate or magnesium carbonate and water, thereby coprecipitating hydroxides, separating and drying them to give a catalyst precursor, and calcining the catalyst precursor for activation at a temperature high enough to give magnesium oxide. The magnesium oxide catalyst obtained in this manner is uniform and exhibits good yields and selectivity for the desired product.

Another process for producing an ortho-alkylating catalyst is disclosed in Japanese Patent Laid-open No. 172352/1985. It consists of dry-mixing manganese carbonate in powder form with magnesium carbonate or basic magnesium carbonate or magnesium hydroxide to give a catalyst precursor, and calcining the precursor. This prior art also discloses that polyphenylene ether resin (PPO resin) may be used as a binder for the catalyst Precursor. With this process, it is possible to prepare the catalyst in a simple manner without resorting to wet process such as suspension mixing or precipitation.

The catalyst disclosed in Japanese Patent Laid-open No. 172352/1985 is claimed to be effective for the production of 2,6-xylenol by ortho-methylation of phenol or o-cresol; however, nothing is mentioned about ortho-methylation of m-cresol or hydroquinone.

The ortho-methylation of m-cresol is disclosed in Japanese Patent Publication No. 29293/1970. The reaction employs a catalyst composed of cerium oxide or a mixture of rare earth elements containing cerium oxide as a major constituent and magnesium oxide. The reaction with this catalyst achieves 76% conversion of m-cresol and gives 2,3-xylenol, 2,5-xylenol, and 2,3,6-trimethylphenol in yields of 20%, 25%, and 22%, respectively. However, it gives 2,6-xylenol which has two dimethyl groups at the ortho position with respect to the hydroxyl group only in low yields.

The ortho-methylation of hydroquinone is described in French Patent No. 2,670,778. The reaction at 440° C. catalyzed by magnesium oxide achieves 52% conversion of hydroquinone and gives methylhydroquinone and dimethylhydroquinone in yields of 40% and 19%, respectively. However, it is poor in selectivity for the desired product, i.e., monomethyl substitution product.

As mentioned above, the magnesium oxide-containing catalyst for ortho-alkylation of phenols is industrially used for production of 2,6-xylenol from phenol, and it has achieved its object to some extent. However, such conventional catalysts are intrinsically subject to deterioration, and hence needs improvement from the industrial point of view.

In addition, the conventional magnesium oxide-containing catalyst for ortho-alkylation of phenols is used under stringent conditions in the case of alkyl-substituted phenols such as m-cresol. Therefore, it is more subject to deterioration, with the result that the thermal decomposition of methanol is accelerated.

Despite several improvements made up to now, there are no satisfactory catalysts that withstand reactions under severe conditions. The catalysts available today gradually lose mechanical strength after continued use under severe conditions and finally disintegrate into powder.

In view of the fact that the known catalyst for ortho-alkylation of phenols is not satisfactory for industrial use, the present inventors carried out a series of researches to develop a long-life catalyst capable of ortho-alkylating phenols with a high selectivity. As the result, it was found that such a catalyst is obtained by calcination from a precursor which is a dry mixture of manganese oxalate, phenolic resin fine particles, and at least one magnesium compound selected from basic magnesium carbonate and magnesium hydroxide. This finding led to the present invention.

SUMMARY OF THE INVENTION

It is an object of the present invention to provide a long-life catalyst for ortho-alkylation of phenols, a precursor thereof, and a process for producing ortho-alkylated phenols (preferably ortho-methylated phenol) by use of said catalyst, said catalyst keeping its catalytic activity for a long time while maintaining its high selectivity throughout the reaction.

BRIEF DESCRIPTION OF THE DRAWING

FIG. 1 is a graph showing the relationship between the reaction temperature and the reaction time in the case of production of 2,3,6-trimethylphenol from m-cresol by ortho-methylation with the catalyst of the invention and the catalyst for comparison. The relationship is a measure of catalyst life.

DESCRIPTION OF THE PREFERRED EMBODIMENTS

Firstly, the invention provides a catalyst precursor convertible Into a catalyst for ortho-alkylation of phenols by calcination, said catalyst precursor comprising a dry mixture of:

(a) manganese oxalate;
(b) phenolic resin fine particles; and
(c) at least one magnesium compound selected from the group consisting of basic magnesium carbonate and magnesium hydroxide;

wherein the content of manganese oxalate is 0.1–10% by weight and the content of phenolic resin fine particles is 0.1–20% by weight, each based on the amount of the magnesium compound.

Secondly, the invention provides a catalyst for ortho-alkylation of phenols, said catalyst being obtained by calcination of the catalyst precursor defined above.

Thirdly, the invention provides a process for producing ortho-alkylated phenols by the gas phase reaction of a phenol with an alkyl alcohol in the presence of the alkylating catalyst defined as above.

As a preferred embodiment, the invention provides a catalyst precursor convertible into a catalyst for ortho-alkylation of phenols, an active catalyst for ortho-methylation of phenols, and a process for producing ortho-methylated phenols.

The catalyst precursor of the invention is a dry mixture of:

(a) manganese oxalate;
(b) phenolic resin fine particles; and
(c) at least one magnesium compound selected from the group consisting of basic magnesium carbonate and magnesium hydroxide;

wherein the content of manganese oxalate is 0.1–10% by weight and the content of phenolic resin fine particles is 0.1–20% by weight, each based on the amount of the magnesium compound.

The precursor is activated upon calcination to provide a catalyst for ortho-alkylation of phenols. The thus obtained catalyst has a high selectivity and a long life in the gas phase ortho-alkylation of phenols. Moreover, the catalyst can be produced in a simple manner with good reproducibility without resorting to the conventional complex wet process.

The catalyst precursor of the invention contains at least one magnesium compound selected from the group consisting of basic magnesium carbonate and magnesium hydroxide.

Basic magnesium carbonate is represented by the formula of:

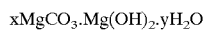

$$xMgCO_3 \cdot Mg(OH)_2 \cdot yH_2O$$

wherein x and y independently denote a numeral of about 3 to 5. It is commonly expressed as $3MgCO_3 \cdot 2Mg(OH)_2 \cdot 3H_2O$.

The basic magnesium carbonate used in the invention is commercially available in the form of fine powder. It may be either heavy type or light type, however, the latter which has a low bulk density is desirable from the standpoint of catalyst life.

The basic magnesium carbonate and magnesium hydroxide may be used alone or in combination with each other, however, it is advantageous to use basic magnesium carbonate alone because it provides a catalyst having high catalytic activity and long life.

The catalyst precursor of the invention contains manganese oxalate as a manganese source. For uniform mixing, it should preferably be in the form of fine powder. According to the invention, the catalyst precursor contains the manganese oxalate in an amount of 0.1–10% by weight, based on the amount of the magnesium compound.

The catalyst precursor of the invention further contains phenolic resin fine particles as a binder for the catalyst precursor. Spherical fine particles with uniform dispersibility and good flowability are desirable. A preferred phenolic resin is a heat-fusible, self-curable phenol-formaldehyde resin which has reactive methylol groups in the molecule, a weight average molecular weight of not less than 3000, and an average particle diameter in the range of 0.1–100 μm. Coarser particles are not desirable because of poor dispersibility and flowability. An example of the phenolic resin fine particles as defined above is "Bellpearl" (registered trademark) available from Kanebo Ltd.

According to the invention, the catalyst precursor contains the phenolic resin fine particles in an amount of 0.1–20% by weight, preferably in an amount of 5–15% by weight, based on the amount of the magnesium compound.

Any well-known molding auxiliary, such as graphite or magnesium stearate may be used in addition to the phenolic resin fine particles to prepare the catalyst precursor. The molding auxiliary may be used in an amount of 0.1–5% by weight based on the amount of the magnesium compound.

The catalyst precursor of the invention may be prepared in the following manner.

Manganese oxalate powder, phenolic resin fine particles, magnesium compound powder, and optionally a molding auxiliary are dry-blended by use of a blender or any other suitable means to form a uniform mixture. The resulting mixture is then compression-molded into a desired shape such as tablets, pellets or cylinders by use of, for example, a tablet machine.

The thus obtained catalyst precursor is finally calcined to impart the catalytic activity. In this way, the desired active catalyst is obtained. The calcination is carried out at least at a temperature of 300° C., preferably at a temperature of 350–500° C. for about 24 hours or less, preferably in the absence of molecular oxygen.

The calcination should preferably be carried out in an atmosphere of an inert gas, such as nitrogen, or under a stream of a vapor of phenols or alkyl alcohols or a mixture thereof which are raw materials for ortho-alkylation of phenols. The atmosphere for the calcination should be free of molecular oxygen so as to avoid combustion which adversely affects the catalytic activity and the mechanical strength and life of the resulting catalyst.

The activation by calcination of the catalyst precursor may be accomplished outside a reactor before it is placed in the reactor or inside a reactor after it has been placed in the reactor. The latter practice is Industrially advantageous. That is, the activation is accomplished by placing the catalyst precursor in a reactor and supplying the reactor with preheated nitrogen or feedstock vapor at a prescribed temperature for heat treatment.

The calcination brings about thermal decomposition of the binder, decarbonation of the manganese oxalate, and dehydration (and decarbonation) of the magnesium compound, with the result that the catalyst precursor is activated and the resulting catalyst has pores formed therein so as to have an increased surface area.

In general, a catalyst should have a surface area greater than 25 m$^2$/g, preferably in the range of 25–500 m$^2$/g. This requirement is easily met if the calcination is carried out under the above specified conditions.

The catalyst obtained as mentioned above is used in the following manner to produce orth-alkylated phenols by ortho-alkylation of phenols, The catalyst of the invention is effective in alkyl substitution on the aromatic ring when used for ortho-alkylation of phenols and is also effective in sustaining the reaction.

According to the invention, the process for producing ortho-alkylated phenols by ortho-alkylation of phenols comprises reacting a phenol with an alkyl alcohol in the gas phase in the presence of the catalyst mentioned above.

Preferred examples of the phenol used in the invention has the formula (I):

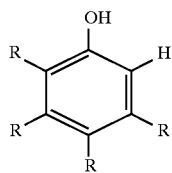

where R's independently denote a hydrogen atom, an alkyl group of 1–12 carbon atoms, a phenyl group, an alkyl substituted phenyl group wherein the alkyl has 1–12 carbon atoms, or a hydroxyl group.

For more preferred phenols, R's in formula (I) above independently denote a hydrogen atom, a methyl group, a hydroxyl group, or an alkyl substituted phenyl group in which the alkyl group has 1–12 carbon atoms with a methyl group being preferred.

Preferred examples of the phenols include phenol, o-cresol, m-cresol, 2,3-xylenol, 2,5-xylenol, 3,4-xylenol, 3,5-xylenol, hydroquinone, and resorcinol. These phenols may be used alone or in combination with one another.

The alkyl alcohol used in the process of the invention is such that it has 1–16 carbon atoms, preferably 1–12 carbon atoms, more preferably 1–6 carbon atoms. It may be a branched-chain, straight-chain, or alicyclic saturated alcohol. Accordingly, the alkyl alcohol used way be exemplified by methyl alcohol, ethyl alcohol, a-propyl alcohol, isopropyl alcohol, n-butyl alcohol, isobutyl alcohol, amyl alcohol, isoamyl alcohol, hexyl alcohol, heptyl alcohol, octyl alcohol, nonyl alcohol, decyl alcohol, lauryl alcohol, cetyl alcohol, cetyl alcohol, cyclohexyl alcohol, or cyclohexylmethyl alcohol. Of these examples, methanol is most preferred. Thus, the process of the invention is most suitable for production of ortho-methylated phenols.

Since the alcohol is usually fed in an excess amount, the alcohol is recycled for reuse after the reaction. The recovered alcohol way contain ether (by-product) corresponding to the alcohol used. This ether may also be used effectively as the alkylating agent.

The process of the invention may be accomplished In the following manner. The process starts with vaporizing a feedstock mixture composed of a phenol and an alkyl alcohol in a preheater and introducing the feedstock vapor into a reactor which has previously filled with the activated catalyst as prepared as mentioned above. In general, the temperature in the reactor is kept at a temperature of 350°–600° C., and preferably at a temperature of 430°–550° C.

More specifically, the reaction temperature varies depending on the product to be produced. It should be comparatively low for production of mono-o-alkyl-substituted phenols, while it should be comparatively high for production of 2,6-dialkyl-substituted phenols. However, the reaction temperature should be not more than 550° C. since the reaction at a temperature more than 550° C. will accelerate thermal decomposition of the alcohol used, resulting in a loss of alcohol.

In order to obtain the desired orth-alkylated product in a maximum yield, it is necessary to use an alcohol in an amount of at least 1 mol, preferably 1–3 mol, per one ortho position in the phenol to be alkylated. By way of example, for production of 2,3,6-trimethylphenol by methylation of m-cresol which has two ortho hydrogen atoms per molecule, it is desirable to use 2–6 mol of methyl alcohol per 1 mol of m-cresol. The use of an alcohol in excess of 3 mol per each or tho position in the phenol to be alkylated increases the yield of the desired mono- or dialkyl-substituted phenols but, at the same time, gives rise to highly alkylated by-products in larger amounts.

The process of the invention employs an alkyl alcohol and a phenol in a specific molar ratio which is established so that the amount of feedstock to be recycled is minimized and the selectivity for the desired ortho-alkylated product is maximized, as the desired product is mono- or dialkyl-phenols which have the alkyl substituent group at one ortho position (position 2) or at two ortho positions (positions 2 and 6) on each aromatic ring of the phenol.

According to the invention, it is preferred that the feedstock mixture composed of a phenol and an alkyl alcohol is passed through a preheater together with water and the vapor of feedstock mixture and the water is introduced into a reactor. The amount of water used is usually not less than 0.5 mol, preferably 1–4 mol, per mol of the phenol. This practice is industrially advantageous because water helps extend the activity of the catalyst.

Further according to the invention, the gas phase catalytic reaction time is in the range of 0.01 to 10 hr$^{-1}$ in terms of liquid space velocity (LHSV) based on the phenol used as a raw material. As in the case of gas phase reaction, the liquid space velocity is defined as the volume of liquid phenol to be fed in one hour per unit amount of the catalyst. The LHSV should be properly adjusted according to the reaction conditions and optimized for the production rate and catalyst life.

The catalytic reaction time should be short (or the liquid space velocity should be large) if the desired product is mono-o-alkylphenol. Conversely, it should be long (or the liquid space velocity should be small) if 2,6-dialkylphenol is to be produced. However, an excessively long catalytic reaction time leads to a low yield per unit amount of the catalyst and subjects the desired product to higher alkylation.

The reaction is carried out usually under the atmospheric pressure; however, the reaction pressure may be varied as desired.

The reaction product is discharged from the reactor in the form of vapor. The vapor is then cooled and condensed. The condensate undergoes oil-water separation. The oil is separated Into individual components, which are further Purified, by ordinary unit operation such as crystallization or distillation.

As set forth above, the catalyst of the invention is obtained from a catalyst precursor by calcination for activation. The catalyst precursor is a dry mixture of manganese oxalate powder, phenolic resin fine particles, and at least one magnesium compound selected from basic magnesium carbonate and magnesium hydroxide. The thus obtained catalyst exhibits high activity and selectivity and has a long life when used for the gas phase ortho alkylation of phenols.

Moreover, the catalyst precursor is a dry mixture so that it immediately gives the active catalyst upon calcination. Thus, the invention easily provides a highly active, highly selective, and long-life catalyst of uniform composition with good reproducibility without requiring complicated technologies as in the conventional wet process.

EXAMPLES

The invention will be described with reference to the following examples, which are not intended to restrict the scope of the invention.

The examples employ "Bellpearl S-870" (from Kanebo Ltd.) as phenolic resin fine particles. Its typical physical properties taken from the catalog are shown below.

Feature: polymeric resin, heat-fusible, self-curable

Specific gravity: 1.24, bulk density: 0.5 g/cc

Particle size: 100 Tyler mesh . . . 99 wt % or more pass 200 Tyler mesh . . . 98 wt % or more pass Average particle diameter: 15–20 μm Gelling time at 180° C.: not measurable Solvent-soluble matter: in boiling methanol . . . 70 wt % in toluene (at room temperature for 1 day) . . . less than 5 wt %

TGA (thermogravimetric analysis; in air): temperature at which weight loss begins . . . 340° C.

TGA (in nitrogen): temperature at which weight loss begins . . . 390° C.

Volume resistivity: $10^{14}\Omega \cdot cm$

The phenolic resin fine particles defined above may be produced by the process disclosed in Japanese Patent Laid-open Nos. 141893/1977, 51019/1986, 177011/1982, and 42077/1978.

The following abbreviations will be used in the examples.

C: m-cresol

H: hydroquinone

35X: 3,5-xylenol

25X: 2,5-xylenol

236T: 2,3,6-trimethylphenol

2346T: 2,3,4,6-tetramethylphenol

235T: 2,3,5-trimethylphenol

2356T: 2,3,5,6-tetramethylphenol

MH: methylhydroquinone

DMH: dimethylhydroquinone

TMH: trimethylhydroquinone

Example 1
Preparation of Catalyst Precursor

A 1-liter beaker was charged with 120.0 g of light basic magnesium carbonate, 13.3 g of phenolic resin fine particles ("Bellpearl S-870" from Kanebo Ltd,), and 4.2 g of manganese oxalate dihydrate ($Mn(COO)_2 \cdot 2H_2O$). The content was thoroughly mixed and dried to give a uniform dry mixture.

The dry mixture was pulverized again and the resulting powder was sieved through a 32-mesh screen. The powder underwent preliminary compression molding by a tablet machine. The tablets were crushed again and the resulting powder was sieved through a 32-mesh screen, The powder was press-molded into cylindrical pellets having a diameter of 5.1 mm and a length of 3.7 mm.

The cylindrical pellets were found to have a bulk density of 1.58 $g/cm^3$ and a crushing strength of 12.3 kg measured with a Kiya meter.

Example 2
Preparation of Catalyst by Calcination of the Catalyst Precursor and ortho-methylation of Phenols in the Presence of the Catalyst In order to evaluate the catalyst performance, 2,3,6-trimethylphenol was prepared using a laboratory reactor (specified below) from m-cresol by ortho-methylation in the presence of the catalyst obtained by calcination of the precursor prepared in Example 1. The calcination of the catalyst precursor was carried out In the reactor under a nitrogen gas stream in the presence of the feedstock mixture.

The reactor was comprised of a preheater for the feedstock mixture, a reactor tube having the vaporization layer, and a receiver to condense and collect the reaction product. The reaction tube was a stainless steel (SUS 304) tube, ½ inch In diameter and 40 cm long, which was placed vertical. The upper part (6 cm) of the reaction tube was filled with ceramic ball fine particles which functioned as a vaporizing layer for the feedstock. Under this layer was a catalyst layer (17 cm) filled with the catalyst precursor (25 ml). The vaporizing layer and the catalyst layer were surrounded by independent electric furnaces so that the layers were individually kept at a desired temperature.

To carry out the reaction, the feedstock mixture was fed to the preheater from a reservoir through a metering pump. In the preheater, the feedstock mixture was heated by an external heater to a temperature high enough for vaporization of the individual feedstock components. The preheater generated a vapor, which was led to the reaction tube through a connecting tube. The vapor was heated to a desired temperature (slightly lower than the reaction temperature) in the above mentioned vaporizing layer. Subsequently, it was led to the catalyst layer where the reaction took place continuously at a prescribed temperature.

The catalyst layer was provided with three thermocouples at the upper, middle and lower parts thereof, so that the temperature in the catalyst layer was accurately controlled within a difference of ±1° C. The reaction product was discharged in the form of vapor from the bottom of the reactor, and was led through a stainless steel pipe and liquefied and collected in the receiver provided with a water cooling tube. Uncondensable matter was introduced to an exhaust gas meter.

The reaction tube was filled with the catalyst precursor (25 ml), which was heated up to 370° C. while a nitrogen gas was passed through the catalyst layer at a flow rate of 6000 ml/hour. This temperature was kept for 15 minutes, and then a mixture of methanol, m-cresol and water (in a ratio of 44/37/19 by weight or 4/1/3 in mol) was introduced at a flow rate of 30.2 ml/hour. This flow rate is equivalent to an LHSV of 1.2 $hr^{-1}$. The LHSV based on m-cresol is 0.45 $hr^{-1}$. This value was used as an index in the following examples for convenience sake.

The reaction was carried out under the atmospheric pressure, and the reaction temperature was adjusted so that the concentration of target product or 2,3,6-trimethyl-phenol remained at 65 1% in the oil layer. The reaction product (2,3,6-trimethylphenol) and by-products were allowed to stand and have its water layer separated. A part of the oil layer was sampled for analysis by gas chromatography. This analysis was performed periodically, i.e., at intervals of 2 hours, so as to keep constant the concentration of 2,3,6-trimethylphenol. Any decrease in the concentration was recovered by raising the reaction temperature by 1°–2° C.

As the reaction proceeded, the reaction temperature was raised in response to the deterioration of the catalyst until it reached 500° C. The time required for the reaction temperature to reach 500° C. was regarded as a measure of catalyst life. The composition of the reaction product was indicated in terms of average value (in % by weight) over the entire reaction time.

The catalyst initially obtained by calcination (for activation) of the catalyst precursor is so active that the reaction temperature can be set low. Thus, the initial reaction temperature is defined as a temperature at which the reaction takes place such that the concentration of 2,3,6-trimethylphenol (target product) in the oil layer is 65±1%. The results are shown in Table 1. The relationship between reaction temperature and reaction time is shown in FIG. 1.

Comparative Example 1

A catalyst precursor in the form of cylindrical pellets was prepared from 120.0 g of basic magnesium carbonate, 13.3 g of polyphenylene ether resin (poly (2,6- dimethyl-1,4-phenylene ether), from General Electric) and 2.7 g of manganese carbonate ($MnCO_3$), in the same manner as in Example 1.

The catalyst precursor was calcined for activation in the same manner as in Example 2. The results are shown in Table 1. The relationship between reaction temperature and reaction time is shown in FIG. 1.

TABLE 1

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 2 | 460 | 2.9 | 22.9 | 65.9 | 2.1 | 1159 |
| Comparative 1 | 475 | 3.2 | 22.7 | 65.2 | 1.9 | 713 |

It is noted that the use of the catalyst of the invention gives rise to the desired product in high selectivity and has a very long life.

Comparative Example 2

The same procedure as in Example 2 was repeated except that the catalyst precursor was calcined in such a way that the temperature of the catalyst layer was raised up to 450° C. over a period of 7 hours and then kept at the temperature for 1 hour during which air was passed through the catalyst layer filled with the catalyst precursor. The resulting catalyst was evaluated in the same manner as in Example 2. The results are shown in Table 2.

TABLE 2

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Comparative 2 | 485 | 0.8 | 26.0 | 65.9 | 0.8 | 400 |

It is noted that the calcination in the presence of molecular oxygen results in a catalyst which needs a high initial reaction temperature and has a shorter catalyst life. Moreover, the calcination in this way burns the phenolic resin fine particles (as the binder for the catalyst precursor), and the resulting catalyst is partly disintegrated Into powder.

Example 3

A catalyst precursor was prepared from 120.0 g of basic magnesium carbonate, 13.3 g of phenolic resin fine particles ("Bellpearl S-870" from Kanebo Ltd.), 4.2 g of manganese oxalate and 3.0 g of graphite powder in the same manner as in Example 1. The resulting catalyst precursor was placed in the reactor and activated there, and the resulting catalyst was evaluated in the same manner as in Example 2. The results are shown in Table 3.

TABLE 3

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 3 | 462 | 2.9 | 23.0 | 66.0 | 1.9 | 1180 |

It is noted that graphite (as the molding auxiliary) added to the catalyst precursor contributes to the long-life, high-performance catalyst.

Example 4

The same procedure as in Example 1 was repeated using the catalyst prepared in Example 1, except that m-cresol in the feedstock was replaced by a mixture of m-cresol and 2,5-xylenol (75/25 by weight). The catalyst performance was evaluated in the same manner as in Example 2. The results are shown in Table 4.

TABLE 4

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 4 | 457 | 3.5 | 24.2 | 65.0 | 1.7 | 1170 |

Example 5

A catalyst precursor was prepared in the same manner as in Example 2 except that light basic magnesium carbonate used in Example 1 was replaced by heavy basic magnesium carbonate. The catalyst precursor was activated and the resultant catalyst performance was evaluated in the same manner as in Example 2. The results are shown in Table 5.

TABLE 5

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 5 | 452 | 3.6 | 22.0 | 66.1 | 2.3 | 1026 |

Example 6

The same procedure as in Example 2 was repeated except that m-cresol was replaced by hydroquinone. The hydroquinone was fed to the preheating layer in the form of 40% solution in ethylene glycol dimethyl ether because it is not readily liquefied due to its high melting point (169° C.) and high boiling point (287° C./730 mmHg). The reaction conditions are as follows, and the results are shown in Table 6.

methanol/hydroquinone/water=4/1/1 in mol
LHSV of hydroquinone=0.3 hr$^{-1}$

TABLE 6

| | Initial Reaction Temperature | Reaction Product (Average) (% by weight) | | | |
|---|---|---|---|---|---|
| | (°C.) | H | MH | DMH | TMH |
| Example 6 | 460 | 57.5 | 23.7 | 11.3 | 2.2 |

Example 7

The same procedure as in Example 2 was repeated except that the LHSV of m-cresol was changed from 0.45 hr$^{-1}$ to 0.6 hr$^{-1}$. The results are shown in Table 7.

TABLE 7

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 7 | 465 | 2.9 | 22.9 | 66.0 | 2.0 | 821 |

Example 8

The same procedure as in Example 2 was repeated except that the molar ratio of methanol/m-cresol/water was changed to 4/1/1. The results are shown in Table 8.

TABLE 8

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 8 | 458 | 2.2 | 23.9 | 65.5 | 2.3 | 738 |

Example 9

A catalyst precursor having a crushing strength of 4 kg was prepared, with the molding pressure reduced. The catalyst precursor was activated In the same manner as in Example 2, and the catalyst performance was evaluated. The results are shown in Table 9.

TABLE 9

| | Initial Reaction Temperature | Reaction Product (Average) (% by weight) | | | | Catalyst Life |
|---|---|---|---|---|---|---|
| | (°C.) | C | 25X | 236T | 2346T | (hour) |
| Example 9 | 464 | 1.6 | 24.9 | 65.4 | 1.8 | 823 |

Comparative Example 3

A catalyst precursor was prepared from 120.0 g of light basic magnesium carbonate, 13.0 g. of polyphenylene ether resin (poly(2,4-dimethyl-1,4-phenylene ether), from General Electric) and 4.2 g of manganese oxalate dihydrate in the same manner as in Example 1. The catalyst precursor was activated and the performance of the resultant catalyst was evaluated in the same manner as in Example 2. The results are shown in Table 10.

TABLE 10

| | Initial Reaction temperature | Reaction Product (Average) (% by weight) | | | | Catalyst Life |
|---|---|---|---|---|---|---|
| | (°C.) | C | 25X | 236T | 2346T | (hour) |
| Comparative 3 | 461 | 3.0 | 24.5 | 64.8 | 2.5 | 728 |

Example 10

The catalyst precursor prepared in Example 9 was activated in the same manner as in Example 2 and the same procedure as in Example 2 was repeated except that m-cresol in the feedstock was replaced by 3,5-xylenol. The catalyst performance was evaluated in the same manner as in Example 2. The reaction conditions are as follows and the results are shown in Table 11.

methanol/3,5-xylenol/water=1/1/0.5 in mol
LHSV of 3,5-xylenol=0.55 hr$^{-1}$

TABLE 11

| | Initial Reaction Temperature | Reaction Product (Average) (% by weight) | | |
|---|---|---|---|---|
| | (°C.) | 35X | 235T | 2356T |
| Example 10 | 450 | 38.1 | 40.7 | 14.4 |

Example 11

A catalyst precursor was prepared from 120.0 g of magnesium hydroxide, 4.3 g of manganese oxalate, and 21.4 g of phenolic resin fine particles ("Bellpearl S-870") in the same manner as in Example 1. The resulting catalyst precursor was calcined and activated in the same manner as in Example 2. The catalyst performance was evaluated. The results are shown in Table 12.

TABLE 12

|  | Initial Reaction Temperature (°C.) | Reaction Product (Average) (% by weight) | | | | Catalyst Life (hour) |
|---|---|---|---|---|---|---|
|  |  | C | 25X | 236T | 2346T |  |
| Example 11 | 467 | 2.1 | 25.3 | 65.3 | 1.0 | 960 |

What is claimed is:

1. A catalyst for ortho-alkylation of phenols obtained by calcination of a catalyst precursor which comprises a dry mixture of:
   (a) manganese oxalate;
   (b) phenolic resin fine particles having a particle diameter of 0.1–100 μm which are obtained by condensation reaction between phenol and formaldehyde; and
   (c) at least one magnesium compound selected from the group consisting of basic magnesium carbonate and magnesium hydroxide;
   wherein the content of manganese oxalate is 0.1–10% by weight and the content of phenolic resin fine particles is 0.1–20% by weight, each based on the amount of the magnesium compound.

2. A catalyst for ortho-alkylation of phenols as defined in claim 1, wherein the catalyst precursor is calcined at temperatures in the range of 300°–500° C. in the absence of molecular oxygen.

3. A catalyst for ortho-alkylation of phenols as defined in claim 1, which has a surface area of 25–500 m²/g.

4. A process for producing ortho-alkylated phenols by the gas phase reaction between an alkyl alcohol and a phenol in the presence of an alkylating catalyst, said catalyst being obtained by calcination of a catalyst precursor which comprises a dry mixture of:
   (a) manganese oxalate;
   (b) phenolic resin fine particles having a particle diameter of 0.1–100 μm which are obtained by condensation reaction between phenol and formaldehyde; and
   (c) at least one magnesium compound selected from the group consisting of basic magnesium carbonate and magnesium hydroxide;
   wherein the content of manganese oxalate is 0.1–10% by weight and the content of phenolic resin fine particles is 0.1–20% by weight, each based on the amount of the magnesium compound.

5. A process for producing ortho-alkylated phenols as defined in claim 4, wherein the phenol has the formula (I):

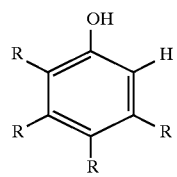

wherein R's independently denote a hydrogen atom, an alkyl group of 1–12 carbon atoms, a phenyl group, or an alkyl substituted phenyl group wherein the alkyl group has 1–12 carbon atoms, or a hydroxyl group.

6. A process for producing ortho-alkylated phenols as defined in claim 4, wherein the reaction between an alkyl alcohol and a phenol is carried out in the gas phase at a temperature of 350°–500° C. in the presence of the ortho-alkylating catalyst.

7. A process for producing ortho-alkylated phenols as defined in claim 4, wherein the alkyl alcohol is methyl-alcohol.

8. A process for producing ortho-alkylated phenols as defined in claim 4, wherein the phenol is at least one selected from the group consisting of phenol, o-cresol, m-cresol, 2,3-xylenol, 2,5-xylenol, 3,4-xylenol, 3,5-xylenol, hydroquinone and resorcinol.

9. A process for producing ortho-alkylated phenols as defined in claim 7, wherein methanol is used in an amount of 2–6 mol per mol of phenols.

10. A process for producing ortho-alkylated phenols as defined in claims 9, wherein water is used in an amount of 0.5–6 mol per mol of phenols.

11. A catalyst precursor convertible into a catalyst for ortho-alkylation of phenols by calcination, said catalyst precursor comprising a dry mixture of:
    (a) manganese oxalate;
    (b) phenolic resin fine particles having a particle diameter of 0.1–100 μm which are obtained by condensation reaction between phenol and formaldehyde; and
    (c) at least one magnesium compound selected from the group consisting of basic magnesium carbonate and magnesium hydroxide; wherein the content of manganese oxalate is 0.1–10% by weight and the content of phenolic resin fine particles is 0.1–20% by weight, each based on the amount of the magnesium compound.

12. A catalyst precursor as defined in claim 11, which is in a molded form.

* * * * *